US006649187B2

(12) United States Patent
Hussain et al.

(10) Patent No.: US 6,649,187 B2
(45) Date of Patent: Nov. 18, 2003

(54) USE OF POLYALKYLAMINE POLYMERS IN CONTROLLED RELEASE DEVICES

(75) Inventors: Munir A. Hussain, Wilmington, DE (US); Arnold J. Repta, Greenville, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/074,385

(22) Filed: Feb. 12, 2002

(65) Prior Publication Data

US 2002/0160047 A1 Oct. 31, 2002

Related U.S. Application Data

(60) Provisional application No. 60/269,243, filed on Feb. 16, 2001.

(51) Int. Cl.[7] .............................. A61K 9/24; A61K 9/30
(52) U.S. Cl. ........................ 424/474; 424/464; 424/473; 424/479; 424/480; 424/489; 424/78.08
(58) Field of Search ................................. 424/474, 464, 424/473, 479, 480, 489, 78.08

(56) References Cited

U.S. PATENT DOCUMENTS

| | | | |
|---|---|---|---|
| 5,348,953 A | 9/1994 | Doherty et al. |
| 5,366,738 A | 11/1994 | Rork et al. |
| 5,556,619 A | 9/1996 | Royce et al. |
| 5,633,344 A | 5/1997 | Figuly |
| 5,667,774 A | 9/1997 | Figuly |
| 5,726,284 A | 3/1998 | Figuly et al. |
| 5,874,522 A | 2/1999 | Figuly et al. |

Primary Examiner—Thurman K. Page
Assistant Examiner—Rachel M. Bennett
(74) Attorney, Agent, or Firm—Burton Rodney

(57) ABSTRACT

The invention provides a method and device for administering an amine drug, such as [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidine-carboxamide), in a sustained release dosage form. The invention includes a pharmaceutical composition and dosage form containing a polyalkylamine polymer and an amine drug. The polyalkylamine polymer is a hydrogel that forms hydrated particles when exposed to an aqueous environment. When mixed with the amine drug in the core of a coated tablet, the polyalkylamine polymer controls the release of the amine drug into an aqueous environment of use. The hydrated particles of the polymer together with the amine drug are released from the tablet core through plural apertures in the surrounding coat.

29 Claims, No Drawings

USE OF POLYALKYLAMINE POLYMERS IN CONTROLLED RELEASE DEVICES

This application claims benefit of No. 60/269,243 filed Feb. 16, 2001.

FIELD OF THE INVENTION

The present invention relates to a controlled release device and in particular to a controlled release device comprising a polyalkylamine polymer for controlling release of an amine drug from the device.

BACKGROUND OF THE INVENTION

Sustained release oral dosage forms of drugs offer the advantages of convenience, improved patient compliance, and reduced peak to trough drug concentration ratio. In addition, they provide lower $C_{max}$ levels and longer $T_{max}$ times than comparable immediate release devices containing the same amount of drug. As a result, controlled release devices generally provide less side effects typically associated with the high plasma peak levels as provided by immediate release devices.

One of the systems that is useful for the delivery of poorly water soluble compounds is the Controlled Release Drug Dispersion Delivery Device disclosed in U.S. Pat. No. 5,366,738. This device comprises a core containing the drug and a polymer that forms gelatinous microscopic particles upon hydration. The core is surrounded by a water insoluble and impermeable coating that contains apertures and adheres to the core. An aqueous fluid from an environment of use enters the core through the apertures and hydrates the polymer to form a dispersion comprising gelatinous particles and the drug. The polymer is a sodium polyacrylate or a carboxypolymethylene. These polymers possess carboxyl functional groups and are negatively charged at physiological pH.

Formula 2: [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) is a novel, monocyclic β-lactam amine drug. It is a highly selective and potent inhibitor of human polymorphonuclear leukocytes (PMN) elastase. Experimental data suggests that [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) may be useful for the treatment of rheumatoid arthritis, among other diseases and disorders. The pharmacokinetic profile of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) suggests that a controlled release device would be well suited for delivering the drug to a patient.

Cation and anion exchange resins have been used for delivering drugs. Generally, these resins are coupled with active agents to form ion pairs. For example, a conventional polyamine resin would be coupled with an acidic drug to form an amine-acid ion pair, which would then be included in a pharmaceutical dosage form. In other words, prior to the present invention, a polyamine resin would not be combined with an amine drug to form a pharmaceutical composition that provides a controlled release of the amine drug.

To date, no formulations that provide the controlled release of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) or its related analogues have contained a polyalkylamine polymer matrix for controlling the delivery of the drug.

SUMMARY OF THE INVENTION

The present inventors have evaluated the device disclosed in the '738 patent and determined that it is not suitable for the controlled delivery of amine drugs, such as [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide), due to the formation of ion pairs or the related incompatibility between the drug and the negatively charged polymer. In addition, the gelatinous particles clog the apertures resulting in incomplete release of drug from the dosage form.

The present invention provides a controlled release device that delivers an amine drug, such as [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide). The controlled release device contains a core prepared from an admixture of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) and a polyalkylamine polymer, such as DMP 504, which is a hydrogel. The core is surrounded by an impermeable water insoluble coat comprising a polymer and a plasticizer. The coat adheres to the core and also includes plural apertures through which hydrated gelatinous particles of polymer containing the amine drug are released into an environment of use.

One aspect of the invention includes a controlled release solid dosage form comprising:

a pharmaceutical composition comprising an amine drug and a polyalkylamine polymer that forms gelatinous particles when hydrated;

a coat surrounding the pharmaceutical composition and comprising a film-forming polymer and plasticizer; and plural apertures in the coat;

wherein the amine drug and polyalkylamine polymer are released through the apertures when the dosage form is placed into an aqueous environment of use, and the dosage form provides a controlled release of the amine drug.

Another aspect of the invention provides a pharmaceutical composition comprising:

an amine drug;

a gel-forming polyalkylamine polymer; and at least one pharmaceutical excipient;

wherein the polyalkylamine polymer controls the release of the amine drug when the pharmaceutical composition is included in a dosage form and exposed to an aqueous environment of use.

Yet another aspect of the invention provides a method of treating a disorder or disease with an amine drug comprising the step of administering to a subject a controlled release dosage form comprising:

a core comprising an amine drug and a polyalkylamine polymer that forms gelatinous particles when hydrated;

a coat surrounding the core and comprising a film-forming polymer and plasticizer; and plural apertures in the coat;

wherein the amine drug and polyalkylamine polymer are released through the apertures when the dosage form is placed into an aqueous environment of use, and the dosage form provides a controlled release of the amine drug.

Embodiments of the Invention

[1] A first embodiment of the invention provides a controlled release solid dosage form comprising:

a pharmaceutical composition comprising an amine drug and a polyalkylamine polymer that forms gelatinous particles when hydrated;

a coat surrounding the pharmaceutical composition and comprising a film-forming polymer and plasticizer; and plural apertures in the coat;

wherein the amine drug and polyalkylamine polymer are released through the apertures when the dosage form is placed into an aqueous environment of use, and the dosage form provides a controlled release of the amine drug.

[2] Another embodiment of the invention provides a controlled release solid dosage form of embodiment [1], wherein the amine drug is the free base or salt form of [S—(R,S)]-2-[4-[[(4-methyl)piperazin-1-yl]carbonyl] phenoxy]-3,3-diethyl-N-[1-(3,4-methylenedioxyphenyl) butyl]-4-oxo-1-azetidinecarboxamide).

[3] Another embodiment of the invention provides a controlled release solid dosage form of any one of embodiments [1] to [2], wherein the polyalkylamine polymer is cross-linked polymeric ammonium salt and comprises groups that link ammonium nitrogen atoms wherein:

about 25% or more of the groups which link ammonium nitrogen atoms are group Y, wherein each Y is independently —C(R$^1$R$^2$)$_b$—; b is an integer of 7 to about 20; and each R$^1$ and each R$^2$ is independently alkylene of about 1 to 20 carbon atoms;

zero to about 75% of the groups which link ammonium nitrogen atoms are group Z wherein Z is a hydrocarbylene radical containing 2 to 50 carbon atoms, the hydrocarbylene radical optionally containing or substituted with one or more hydroxyl, ether, ester, amino, thioether, keto, silyl group or heterocyclic rings;

about 25% or more of the ammonium nitrogen atoms are secondary ammonium nitrogen atoms; and said cross-linked polymeric ammonium salt is insoluble in water.

[4] Another embodiment of the invention provides a controlled release solid dosage form of any one of embodiments [1] to [3], wherein the polyalkylamine polymer is a polymer of the Formula 1:

$$\begin{array}{c}\text{Formula I}\\ \left[\begin{array}{c}-(CH_2)_6NH_2^+(CH_2)_{10}NH^+(CH_2)_6NH_2^+(CH_2)_{10}NH_2^+(CH_2)_6NH^+(CH_2)_{10}NH_2^+(CH_2)_6NH_3^+\\ | \qquad\qquad\qquad\qquad | \qquad\qquad\qquad\qquad |\\ (CH_2)_{10} \qquad\qquad\qquad (CH_2)_{10} \qquad\qquad\qquad NH_2^+\\ | \qquad\qquad\qquad\qquad | \qquad\qquad\qquad\qquad |\\ H_3N(CH_2)_6NH^+(CH_2)_{10}NH^+(CH_2)_6NH_2^+(CH_2)_{10}NH^+(CH_2)_6NH^+(CH_2)_{10}NH_2^+(CH_2)_6\\ | \qquad\qquad\qquad\qquad\qquad |\\ (CH_2)_{10} \qquad\qquad\qquad\qquad (CH_2)_{10}NH_2^+(CH_2)_6NH_2\\ |\\ -(CH_2)_{10}NH_2^+(CH_2)_6NH^+(CH_2)_{10}NH^+(CH_2)_6NH_2^+(CH_2)_{10}NH^+(CH_2)_6NH^+(CH_2)_{10}NH_2^+(CH_2)_6\\ | \qquad\qquad\qquad\qquad\qquad\qquad |\\ (Cl^-)_m \quad\; m=\text{Number of nitrogen cations} \quad\quad NH_3^+\end{array}\right]_n\end{array}$$

wherein n is at least one; m is at least equal to the number of quaternary amines; and the ends are independently capped with amine or hydroxyl groups.

[5] Another embodiment of the invention provides a controlled release solid dosage form of any one of embodiments [1] to [4], wherein the polyalkylamine polymer is DMP 503 or DMP 504.

[6] Another embodiment of the invention provides a controlled release solid dosage form of any one of embodiments [1] to [5], wherein the polyalkylamine polymer has a swell factor of at least about 4.

[7] Another embodiment of the invention provides a controlled release solid dosage form of any one of embodiments [1] to [6], wherein the polyalkylamine polymer comprises about 15–25% primary ammonium nitrogen atoms, about 40–60% secondary ammonium nitrogen atoms, about 15–25% tertiary ammonium nitrogen atoms and less than about 5% quaternary ammonium nitrogen atoms.

[8] Another embodiment of the invention provides a controlled release solid dosage form of any one of embodiments [1] to [7], wherein at least one nitrogen atom in the polyalkylamine polymer is further substituted with the group Q which is a hydrocarbyl group containing 1 to 50 carbon atoms, and optionally containing one or more hydroxy, ether, amino, thioether, keto, silyl groups or heterocyclic rings.

[9] Another embodiment of the invention provides a controlled release solid dosage form of any one of embodiments [1] to [8], wherein the polyalkylamine polymer is made in the presence of a template.

[10] Another embodiment of the invention provides a controlled release solid dosage form of any one of embodiments [1] to [9], wherein the amine drug is released over a period of at least 3 hours or a period of 3–24 hours after exposure to an aqueous environment.

[11] Another embodiment of the invention provides a controlled release solid dosage form of any one of embodiments [1] to [10], wherein the film-forming polymer is selected from the group consisting of polyvinylchloride, cellulose acetate, cellulose acetate butyrate, ethylcellulose, and a combination thereof.

[12] Another embodiment of the invention provides a controlled release solid dosage form of any one of embodiments [1] to [11], wherein the plural apertures are at least about 100 μm in diameter.

[13] Another embodiment of the invention provides a controlled release solid dosage form of any one of embodiments [1] to [12], wherein the dosage form comprises at least about 2 apertures.

[14] Another embodiment of the invention provides a controlled release solid dosage form of any one of embodiments [1] to [13], wherein the polyalkylamine polymer is a particulate hydrogel that forms hydrated particles when exposed to an aqueous environment.

[15] Another embodiment of the invention provides a controlled release solid dosage form of embodiment [14], wherein 50% of the hydrated particles are about 100 μm in diameter.

[16] Another embodiment of the invention provides a controlled release solid dosage form of any one of embodiments [1] to [15], wherein the amine drug is released into an environment of use according to a release profile approximating the following:

| Time (h) | Amount Release (% wt.) |
|----------|------------------------|
| 0.5      | 0–10                   |
| 1.0      | 1–15                   |
| 2.0      | 5–25                   |
| 4.0      | 10–30                  |
| 8.0      | 20–50                  |
| 12       | 30–70                  |
| 16       | 50–90                  |
| 20       | 60–95                  |
| 24       | 70–100                 |

[17] Another embodiment of the invention provides a controlled release solid dosage form of any one of embodiments [1] to [16], wherein the plasticizer is selected from the group consisting of diethylphthalate, dibutylsebacate, or triethylcitrate.

[18] Another embodiment of the invention provides a controlled release solid dosage form of any one of embodiments [1] to [17], wherein the pharmaceutical composition further comprises at least one pharmaceutical excipient selected from the group consisting of a release-modifying agent, bulking agent, processing agent, antioxidant, acidifying agent, alkalizing agent, buffering agent, preservative, adsorbent, sweetening agent, antiadherent, binder, lubricant, diluent, direct compression excipient, glidant, lubricant, opaquant, polishing agent, disintegrant, flavorant, colorant, and osmotic agent.

[19] Another embodiment of the invention provides a controlled release solid dosage form of any one of embodiments [1] to [18], wherein the film-forming material forms an impermeable water insoluble coat.

[20] Another embodiment of the invention provides a pharmaceutical composition comprising:
    an amine drug;
    a gel-forming polyalkylamine polymer; and
    at least one pharmaceutical excipient;
    wherein the polyalkylamine polymer controls the release of the amine drug when the pharmaceutical composition is included in a dosage form and exposed to an aqueous environment of use.

[21] Another embodiment of the invention provides a pharmaceutical composition of embodiment [20], wherein the amine drug is the free base or salt form of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide).

[22] Another embodiment of the invention provides a pharmaceutical composition of an one of embodiments [20] to [21], wherein the polyalkylamine polymer is cross-linked polymeric ammonium salt and:
    about 25% or more of the groups which link ammonium nitrogen atoms are group Y, wherein each Y is independently —C($R^1R^2$)$_b$—; b is an integer of 7 to about 20; and each $R^1$ and each $R^2$ is independently alkylene of about 1 to 20 carbon atoms;
    zero to about 75% of the groups which link ammonium nitrogen atoms are group Z wherein Z is a hydrocarbylene radical containing 2 to 50 carbon atoms, the hydrocarbylene radical optionally containing or substituted with one or more hydroxyl, ether, ester, amino, thioether, keto, silyl group or heterocyclic rings;
    about 25% or more of the ammonium nitrogen atoms are secondary ammonium nitrogen atoms; and
    said cross-linked polymeric ammonium salt is insoluble in water.

[23] Another embodiment of the invention provides a pharmaceutical composition of an one of embodiments [20] to [22], wherein the polyalkylamine polymer is a polymer of the Formula 1:

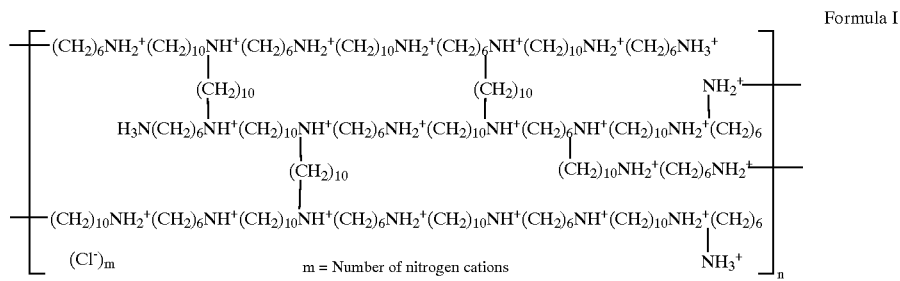

Formula I wherein n is at least one; m is at least equal to the number of quaternary amines; and the ends are independently capped with amine or hydroxyl groups.

[24] Another embodiment of the invention provides a pharmaceutical composition of an one of embodiments [20] to [23], wherein the polyalkylamine polymer is DMP 503 or DMP 504.

[25] Another embodiment of the invention provides a pharmaceutical composition of an one of embodiments [20] to [24], wherein the polyalkylamine polymer has a swell factor of at least about 4.

[26] Another embodiment of the invention provides a pharmaceutical composition of an one of embodiments [20] to [25], wherein the polyalkylamine polymer comprises about 15–25% primary ammonium nitrogen atoms, about 40–60% secondary ammonium nitrogen atoms, about 15–25% tertiary ammonium nitrogen atoms and less than about 5% quaternary ammonium nitrogen atoms.

[27] Another embodiment of the invention provides a pharmaceutical composition of an one of embodiments [20] to [26], wherein at least one nitrogen atom in the polyalkylamine polymer is further substituted with the group Q which is a hydrocarbyl group containing 1 to 50 carbon atoms, and optionally containing one or more hydroxy, ether, amino, thioether, keto, silyl groups or heterocyclic rings.

[28] Another embodiment of the invention provides a pharmaceutical composition of an one of embodiments [20] to [27], wherein the polyalkylamine polymer is made in the presence of a template.

[29] Another embodiment of the invention provides a pharmaceutical composition of an one of embodiments [20]

to [28], wherein the polyalkylamine polymer is a particulate hydrogel that forms hydrated particles when exposed to an aqueous environment.

[30] Another embodiment of the invention provides a pharmaceutical composition of an one of embodiments [20] to [29], wherein 50% of the hydrated particles are about 100 μm in diameter.

[31] Another embodiment of the invention provides a pharmaceutical composition of an one of embodiments [20] to [30], wherein the at least one pharmaceutical excipient selected from the group consisting of a release-modifying agent, bulking agent, processing agent, antioxidant, acidifying agent, alkalizing agent, buffering agent, preservative, adsorbent, sweetening agent, antiadherent, binder, lubricant, diluent, direct compression excipient, glidant, lubricant, opaquant, polishing agent, disintegrant, flavorant, colorant, and osmotic agent.

[32] Another embodiment of the invention provides a method of treating a disorder or disease with an amine drug comprising the step of administering to a subject the dosage form of any one of embodiments [1] to [19].

[33] Another embodiment of the invention provides a method of treating a disorder or disease with an amine drug comprising the step of administering to a subject the pharmaceutical composition of any one of embodiments [20] to [31].

Further specific embodiments of the invention include those wherein: 1) the amine drug is [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) (DuPont Pharmaceutical Co., Wilmington, Del.); 2) the polyalkylamine polymer is DMP 503 or DMP 504 (DuPont Pharmaceutical Co., Wilmington, Del.); 3) the amine drug is released over a period of at least 3 hours or a period of 3–24 hours after exposure to an aqueous environment; 4) the polyalkylamine polymer is cross-linked polymeric ammonium salt of the formula 1; 5) the polyalkylamine polymer is a polymer of the Formula 1; 6) the film-forming polymer is selected from the group consisting of polyvinylchloride, cellulose acetate, cellulose acetate butyrate, ethylcellulose, and a combination thereof; 7) the polyalkylamine polymer has a swell factor of at least about 4; 8) the polyalkylamine polymer comprises about 15–25% primary ammonium nitrogen atoms, about 40–60% secondary ammonium nitrogen atoms, about 15–25% tertiary ammonium nitrogen atoms and less than about 5% quaternary ammonium nitrogen atoms; 9) at least one nitrogen atom in the polyalkylamine polymer is further substituted with the group Q which is a hydrocarbyl group containing 1 to 50 carbon atoms, and optionally containing one or more hydroxy, ether, amino, thioether, keto, silyl groups or heterocyclic rings; 10) the polyalkylamine polymer is made in the presence of a template; 11) the plural apertures are at least about 100 μm in diameter; 12) the dosage form comprises at least about 2 apertures; 13) the polyalkylamine polymer is a particulate hydrogel that forms hydrated particles when exposed to an aqueous environment; 14) 50% of the hydrated particles are about 100 μm in diameter; 15) the amine drug is released into an environment of use according to a release profile as described herein; and/or 16) the film-forming material forms an impermeable water insoluble coat.

DETAILED DESCRIPTION OF THE INVENTION

As used herein, a polyalkylamine polymer is a polymeric material containing plural amine functional groups. When not in its salt form, the polyalkylamine polymer is a strongly basic anion-exchange polymer containing randomly distributed primary, secondary, tertiary, and quaternary amine functional groups. The polyalkylamine polymer is present in its free-base and/or pharmaceutically acceptable salt form. Suitable polyalkylamine polymers are disclosed in U.S. Pat. No. 5,667,774, No. 5,874,522, No. 5,726,284, No. 5,556,619, No. 5,633,344 and PCT International Publication No. WO 94/0496, the entire disclosures of which are hereby incorporated by reference. Other known polyalkylamine polymers that form a gel structure when hydrated may be useful in the formulation of the invention. The Formula 1 polymer is generally formed by a condensation reaction between a polyamine and a bifunctional amine acceptor, for example. The Formula 1 polymer comprises a mixture of primary, secondary, tertiary and quaternary amine groups. When present in their salt forms, the primary, secondary and tertiary amines are ammonium nitrogens. The ratio of the different amine group types varies according to the molar ratio of the polyamine, and the identity of the polyamine and bifunctional amine acceptor.

As used herein, the term "hydrocarbylene" includes any hydrocarbon group such as, by way of example and without limitation, alkyl, alkenyl, alkynyl, carbocycle, cycloalkyl, alkylcycloalkylalkyl, alkylcarbocycle, or carbocyclealkyl groups, which are connected by two bonds to the rest of the structure of cross-linked polymer of the present invention. By "in-chain" ether, ester, amino, thioether, keto, silyl groups, or heterocyclic rings it is meant that the hydrocarbylene group contains one or more (preferably 1–5 groups, independently selected) in-chain —O—, —OC(=O)—, —C(=O)O—, —NH—, —N($C_1$-$C_{10}$ alkyl)—, —S—, —C(=O)—, —SiH($C_1$-$C_{10}$ alkyl)—, —Si($C_1$-$C_{10}$ alkyl)$_2$—, or -(heterocycle)-groups. By "substituent" hydroxy, ether, amino, thioether, keto, silyl groups, or heterocyclic rings it is meant that the hydrocarbolene group is substituted with one or more (preferably 1–5, independently selected) —OH, —O($C_1$-$C_{10}$ alkyl), —($C_1$-$C_{10}$ alkyl)O ($C_1$-$C_{10}$ alkyl), —NH$_2$, —NH($C_1$-$C_{10}$ alkyl), —NH ($C_1$-$C_{10}$ alkyl)$_2$, —SH, —S($C_1$-$C_{10}$ alkyl), —($C_1$-$C_{10}$ alkyl)S($C_1$-$C_{10}$ alkyl), =O, ($C_1$-$C_{10}$ alkyl), —SiH($C_1$-$C_{10}$ alkyl)$_2$, or -(heterocycle) groups.

As used herein, the term "hydrocarbyl" includes any hydrocarbon group such as, by way of example and without limitation, alkyl, alkenyl, alkynyl, carbocycle, cycloalkyl, alkylcycloalkylalkyl, alkylcarbocycle, or carbocyclealkyl groups, which are connected by one bond to the rest of the structure of cross-linked polymer of the present invention. Such hydrocarbyl group may contain an in-chain or substituent group as described above for a hydrocarbolene group.

Unless they are end groups, the nitrogen atoms of the ammonium salts (ions) of the polymer are located between polymer segments. At least about 25% of these groups, designated herein as Y, linking these nitrogen atoms are independently selected from n-alkylene groups having 7 to about 20 carbon atoms. By an n-alkylene group herein is meant the group —(CH$_2$)$_b$— wherein b in this instance is 7 to about 20. This n-alkylene group Y may also be substituted with alkyl groups, and is then in effect a branched alkylene group. A specific embodiment of the n-alkylene group has 7 to 14 carbon atoms, or 9 to 12 carbon atoms. Other hydrocarbylene groups, such as ones wherein the distance between nitrogen atoms is equivalent to at least 7 methylene groups, are also suitable.

The other nitrogen atoms of the ammonium salts are connected by hydrocarbylene groups, designated herein as Z, containing 2 or more carbon atoms, or 2 to 50 carbon atoms, i.e., there must be at least two carbon atoms between the nitrogen atoms. By "hydrocarbylene" is meant a divalent radical containing only carbon and hydrogen. The hydrocarbylene group Z may be substituted by various substituents. Suitable substituents include ether, ester amino, thioether, keto, silyl group or heterocyclic rings. In specific embodiments, the substituents are ether or amino. In specific embodiments, the hydrocarbylene group is saturated. In specific embodiments, the hydrocarbylene group Z is an n-alkylene group containing 2 to 14 carbon atoms. In other specific embodiments, the substituents contain 1 to 50 carbon atoms, or 1–30 carbon atoms.

As used herein, "alkyl" is intended to include both branched and straight-chain saturated aliphatic hydrocarbon groups having the specified number of carbon atoms (the number of carbon atoms may be specified, for example, as "$C_1$–$C_{10}$" to denote alkyl having 1 to 10 carbon atoms). "Alkenyl" is intended to include hydrocarbon chains of either a straight or branched configuration and one or more unsaturated carbon—carbon bonds which may occur in any stable point along the chain, such as ethenyl, propenyl and the like; and "alkynyl" is intended to include hydrocarbon chains of either a straight or branched configuration and one or more triple carbon—carbon bonds which may occur in any stable point along the chain, such as ethynyl, propynyl and the like.

The terms "alkylene", "alkenylene", "phenylene", "cycloalkylene" and the like, refer to alkyl, alkenyl, phenyl, and cycloalkyl groups, respectively, which are connected by two bonds to the rest of the structure of the cross-linked polymer of the present invention. Such groups may alternatively and equivalently be denoted as -(alkyl)-, -(alkenyl)-, -(phenyl)-, -(cycloalkyl)-, and the like, respectively.

"Alkoxy" represents an alkyl group of indicated number of carbon atoms attached through an oxygen bridge; "alkylthio" represents an alkyl group of indicated number of carbon atoms attached through an sulfur bridge; "monoalkylamino" and "dialkylamino" represents a N atom substituted with 1 or 2 alkyl groups, respectively, of the indicated number of carbon atoms; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic ring" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, .beta.-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

By "cross-linked" is meant a polymer that has a network structure. A common test to determine if a polymer is cross-linked is to try to dissolve the polymer in a liquid that is normally a solvent for that polymer. Linear or branched, but not cross-linked, polymers will dissolve in the solvent. Cross-linked polymers do not dissolve, although they may swell to some degree. The polymeric ammonium salts described herein, when not cross-linked, are generally soluble in water or other polar solvents. When cross-linked, the polymeric ammonium salts swell in water, often to form gel-like particles.

The extent to which the polymeric ammonium salt swells is expressed as its swell factor. The swell factor is taken as the ratio of the weight of water imbibed by the polymer divided by the weight of the polymer used. A polymeric ammonium salt having a swell factor of at least about 4, about 5 to 40 or about 15 to 35 is particularly suitable.

The polyalkylamine polymer is used as either its freebase, ammonium salt, or mixture thereof. By "ammonium salt" or "ammonium ion" is meant a nitrogen atom bonded to four other atoms. For example, in the ammonium ion itself, the nitrogen is bonded to four hydrogen atoms. In a primary ammonium ion, the nitrogen atom is bonded to three hydrogen atoms and one carbon atom. In a secondary ammonium ion, the nitrogen is bonded to two carbon atoms and two hydrogen atoms. In a tertiary ammonium ion, the nitrogen is bonded to three carbon atoms and one hydrogen atom, and in a quaternary ammonium ion, the nitrogen is bonded to 4 carbon atoms. In the polymeric ammonium salts of the present invention, at least 25%, or at least about 40%, of the ammonium nitrogen atoms are secondary ammonium nitrogen atoms. In one embodiment, primary ammonium nitrogen atoms comprise 15 to 25%, secondary ammonium nitrogen atoms comprise 40–60%, tertiary ammonium nitrogen atoms comprise 15 to 25% and quaternary ammonium nitrogen atoms comprise less than 5% of all the total ammonium nitrogen atoms in the polymer. The determination of what types of ammonium nitrogen atoms are present is described in U.S. Pat. No. 5,667,774.

Each ammonium salt comprises a nitrogen atom having one positive charge and a counter ion. The counterion may be any negative ion which conjugate (Bronsted) acid is capable of protonating the conjugate base of the ammonium salt. The ammonium salt will include a pharmaceutically acceptable salt form. The counterion should be biologically compatible and not cause substantial undesired physiological changes when administered in a dosage form. Suitable biologically compatible counterions include chloride, bromide, iodide, sulfate, phosphate, acetate, ascorbate, carbonate, bicarbonate, nicotinate, salicylate, tartrate and citrate. A generally preferred salt form is the chloride salt.

The polyamines polymers (and their salts), as described herein, may have nitrogen atoms that are further substituted, typically by reaction with (substituted) alkyl halides to form for example, secondary amine (salts) from primary amines, and tertiary amines from secondary amines. However, in the resulting polyamine (salt), 25% or more of the amino (ammonium) nitrogen atoms are generally secondary. The group Q which is further substituted on a nitrogen is a hydrocarbyl group containing 1 to 50 carbon atoms, and may contain one or more hydroxy, ether, amino, thioether, keto, silyl groups or heterocyclic rings. Generally, Q contains 1–30 carbon atoms.

Some embodiments of the polyamine polymer can be made as described in U.S. Pat. No. 5,667,774, No. 5,874, 522, No. 5,726,284, No. 5,556,619, No. 5,633,344 and PCT International Publication No. WO 94/0496. The polyamine polymers disclosed therein are generally made as follows. A bifunctional amine acceptor is reacted with a bifunctional amine to form the polyalkylamine polymer. For example, an organic dihalide is reacted with a diamine, both of whose amine groups are primary amines. For the purposes of this discussion, the dihalide can be represented by X—Y—X and/or X—Z—X, where X is chlorine, bromine or iodine, and Y or Z is the group to which both halogen atoms are bound. The diamine is represented by $H_2N$—Y—$NH_2$ and/or $H_2N$—Z—$NH_2$, where Y or Z is the group to which the two amino groups are bound. In order to obtain the desired polymer, at least some of the dihalide and/or some of the diamine must contain Y as described above. In some embodiments, the Y or Z group should be of such a size that the halogen atoms are the equivalent of about 7 or more methylene groups apart. Groups Y and Z may be selected independently at each position in a particular polymer.

Useful dihalides include, but are not limited to, 1,10-dibromodecane, 1,12-dibromododecane, 1,8-dibromooctane, 1,18-dibromooctadecane, 1,9-dibromononane, 1,7-dibromoheptane, 1,8-diiodooctane, 1,8-dibromo-3-ethyloctane, and 1,9-dibromodecane. Useful diamines include, but are not limited to, ethylene diamine, 1,6-diaminohexane, 1,12-diaminododecane, 2-methyl-1,5-diaminopentane, 1,4-bis(aminomethyl)cyclohexane, 1,3-diaminopentane, diethylenetriamine, 1,4-bis(3-aminopropyl)piperazine, 1,4-cyclohexanediamine, 5-amino-1-aminomethyl-1,3,3-trimethylcyclohexane. 1,3-propanediamine, 1,4-butanediamine, 1,5-pentanediamine, 1,7-heptanediamine, 1,8-diaminooctane, 1,9-diaminononane, 1,10-diaminodecane, 1,11-diaminoundecane, 2-hydroxy-1,3-propanediamine, and 4,4'-methylene-bis(cyclohexylamine). More than one type of diamine and/or dihalide may be used.

The polymeric ammonium salts can also be made by reaction of a diamine with a diepoxide. In this case, it is the diamine in which the nitrogen atoms are connected by an n-alkylene group (which may be alkyl substituted) containing 7 to about 20 carbon atoms. After synthesis of these polymers, the ammonium salts are formed by neutralization of the amines with acids.

The polymeric ammonium salts can be made from the above diamines and dihalides or diepoxides by dissolving the reactants in a solvent, typically a polar solvent such as methanol, ethanol, N,N-dimethylformarnide, N,N-dimethylacetamide, dimethylsulfoxide, tetrahydrofuran, water, and mixtures thereof. Reaction temperature is generally not critical, and temperatures ranging from ambient to the boiling point of the solvent (or lower boiling ingredient) are useful. Depending on the temperature, reactants and solvent, reaction is complete in a few minutes to a few days, typically about 1 to 8 hours. The reaction may be followed by observing the viscosity of the solution, which will gradually increase until a gel is formed or the polymeric product precipitates. If the polymer does not precipitate (when it can be isolated by filtration), the polymer can be recovered from the resulting gel by adding the gel to a solvent in which the polymer is not soluble, for example tetrahydrofuran, in which the polymer will precipitate.

In the polymerization, the reactant monomer concentrations of the reactant solutions, when taken individually, generally range from 5% to 60% by weight (wt) relative to the total reaction solution weight. After mixing of the reactant solutions, the overall monomer concentration in the reactor is 5% to 60% by wt. where the preferred operating range is 35% to 45% by wt. If the reactants are dissolved together in the solvent, the overall solids loading, or monomer concentration, in the reactor is generally 5% to 60% by wt., or generally 35% to 45% by wt.

The mole ratio of reactants as well is controlled during the polymerization. Approximately equimolar amounts of the diamine and bifunctional amine acceptor are reacted. A suitable range for the mole ratio of the diamine compound to bifunctional amine acceptor is about 0.9–1.4, or about 1.0–1.20.

In general, the polymerization step (including gelation) is conducted in such a manner as to allow control of the reactant mole ratio, temperature, time, solvent composition, reagent feed rate, order and mode of reagent addition, monomer concentration, mixing and other reaction variables. The polymeric ammonium salts can be made from the above described diamines and bifunctional amine acceptors (for example, dihalides or diepoxides) by dissolving the reactant monomers, either separately or together, in a suitable solvent, typically a polar solvent, such as described below. The reactants are then mixed under controlled conditions using a suitable reactor. Following heating and agitation, the reaction mixture forms a gel or granular crumb-like solid, i.e. undergoes gelation as discussed below. At this point, the crude polymeric ammonium salts are ready for purification, ion exchange, size reduction, and/or drying if so desired.

By "gelation" is meant the point at which the polymer becomes insoluble due to cross-linking. In a suitable solvent, a swollen gel will form at the point at which the polymer becomes insoluble. The gel may become a crumb-like solid upon breaking either by agitation in the reactor or high shear milling, as described below.

The suitable solvent used in the polymerization reaction step may be a single compound or a mixture of compounds. All of the starting materials that react to form the cross-linked polymer should be soluble in the solvent. Useful solvents include polar compounds such as N,N-dimethylformamide, N,N-dimethylacetamide, dimethylsulfoxide, hexamethyl phosphoramide (HMPA), N-methyl pyrrolidone (NMP), isopropanol, methanol, ethanol and other lower alcohols and lower ethers. These may be used in combination with each other or alone.

The polymerization reaction is generally mixed or agitated during the reaction period. The intensity of reaction mixing can be changed during different stages of the reaction. Generally, the reaction mixture is well stirred prior to the gel point or gelation. Mixing during and after gelation is not critical on the small scale; however, on the large multikilogram reaction scale, mixing during and after the gelation becomes important. Mixing during the polymerization reaction also facilitates product removal by preventing the polymer from forming a single solid mass in the reactor and the gel particle size can be controlled by the judicious selection of the mixing speeds. In general, the faster the mixing during and after gelation, the smaller is the resulting gel particle size of the polymeric ammonium salt present in the reactor.

The rate and order of reactant addition to the reactor may be controlled. In general, the reactants may be added either concurrently or sequentially in any order separately into the reactor. When added sequentially, it is the rate of addition of the second reactant to the first reactant in the reactor, is generally sufficiently fast so as to minimize addition of the second monomer after gelation of the reaction mixture. When the reactant monomers are added concurrently to the reactor, the reactant rate of addition is generally not critical. The reactants may be added at the same rate (based on equivalents, volumes, and/or weights) where completion of addition for both reactants is simultaneous ("cofeeding"), or the reactants may be added at different rates such that the completion of addition for either reactant continues beyond completion of addition of the other, but generally prior to gelation.

The performance of polyalkylamine polymer may be improved by carrying out the polymerization in the presence of a "template". The terms "template", "template material" or "templating agent", as used herein, means a chemical substance which is substantially inert to the reaction, reaction starting materials and products, and that effects an enhancement of the drug delivery properties of the polymer product.

Scanning electron micrographs of some embodiments of the cross-linked polyalkylamine polymer of the invention prepared in the presence of the templates generally show a porous or reticulated structure with pore size ranging from about 1 to 300 microns depending on the overall particle size of the cross-linked polymer. In contrast, the same cross-linked polymeric materials prepared in the absence of templates generally do not exhibit porous structures.

For convenience, the templates may be added at the beginning of the cross-linking and/or polymerization reaction. Normally, the template will remain in the gel until it is removed, as by solvent extraction.

If a template is used, it may be soluble, partially soluble, or insoluble in the polymerization reaction medium. However, the template should be soluble in a solvent (not necessarily the solvent used in the cross-linking process) so that it can be separated from the cross-linked polymer that is produced in the instant process. This separation would occur during a purification step. For instance, the template may be separated from the cross-linked polymer by extraction of the cross-linked polymer with a solvent in which the template is soluble. This can be the same solvent as used in the instant process if a soluble polymer is used as the template. Solvent extraction also encompasses use of a solvent as the extractant which chemically converts the template to a soluble material, while not substantially, affecting the polymer structure of the cross-linked polymer. For example, an aqueous acid, such as aqueous HCl, may be used to convert the template to a soluble material. HCl may also convert the polymeric ammonium salt to a chloride. Thus, the solvent used to remove the template from the cross-linked polymer of the invention may change the salt form of the cross-linked polymer. After extraction of the template, the cross-linked polymer may, if desired, be isolated in pure form by removal of the extraction solvent, as by filtration and/or evaporation in air or under vacuum.

Templates which are insoluble in the reaction medium may have a particle size of less than about 1000 microns (measured as being able to pass through a sieve of that size), or less than about 600 microns. Such particle sizes may be made, for example by grinding a solid substance, or by dispersing a liquid substance (including a polymer) in the solvent beforehand using high shear. Dispersion of the insoluble template during the process can be maintained by simple means, such as agitation.

The template should not interfere in the reaction(s), as described earlier, which form the cross-linked polymer of the invention, and should not, itself, become part of the chemical structure of the cross-linked polymer. The template should also not strongly coordinate with any of the starting materials for the cross-linked polymer or the cross-linked polymer itself.

Polymers for use as templates include both natural and synthetic polymers, including both thermoplastics and elastomers. Useful polymers include, but are not limited to, polyacrylates, polymethacrylates, polyvinylpyrrolidone, poly(vinyl acetate), various starches, corn products such as amaizo, amylose and zein, pectin, alkoxylated celluloses, polyesters and polyethers.

Representative organic polymeric template substances also include cellulose polymers (such as ethylcellulose, hydroxypropylcellulose, methylcellulose, and hydroxypropyl methylcellulose), polyethylene glycol, proteins, nucleic acids, albumin, gelatin, starch, collagen, dextran and modified dextrans, polysaccharides, polylactide/polyglycolide, polyalkylcyanoacrylates, polyacrylamide, polysorbates, polyethylene ethers and esters, and polyoxyethylene/polyoxypropylene block polymers.

Suitable templates may also include natural and synthetic gums (such as acacia, tragacanth, or sodium alginate), sodium oleate, sodium stearate, magnesium stearate, sodium benzoate, sodium acetate, agar, bentonite, xanthan gum, phospholipids (such as cholesterol, stearylamine, or phosphatidylcholines), and soluble polymers such as polyvinylpyrrolidone, pyran copolymer, polyhydroxypropylmethacrylamide-phenol, polyhydroxyethylaspartamidephenol, or polyethyleneoxide-polylysine substituted with palmitoyl residues. Other polymers useful as templates may include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and cross-linked or amphipathic block copolymers of hydrogels. Specific polymers include poly(2-hyroxyethyl methacrylate), polyvinylpyrrolidone, poly (vinyl acetate), potato starch, wheat starch, pea starch, gellan gum, welan gum, rhamsam gum, xanthan gum, amaizo, amylose, zein, pectin, hydroxypropyl cellulose, carboxymethylcellulose, polyester glycols and polyether glycols.

Nonpolymeric templates include, but are not limited to: mono- or disaccharides, such as galactose, lactose, trehalose, and sucrose; steroid derivatives, cholesterol derivatives, bile acid derivatives, such as cholesterol esters, sodium cholate, methyl cholate, and cholesteryl chloride; and inorganic materials and salts, such as metal halides (for example, KCl and NaCl), metal carbonates, borates and phosphates (and salts thereof). Also useful as templates are metal carboxylates, such as acetates, propanoates, butyrates, salicylates, gluconates, ascorbates, citrates, and salts thereof. Inorganic material useful as a template in the present invention includes borates and phosphates (and salts thereof) in the form of monomeric salts or as polymeric forms, or as mixtures of monomeric and polymeric forms. The inorganic material may be in a crystalline and amorphous form, or a mixture of crystalline and amorphous forms.

One or more of the above-described templates may be used in combination in a particular polymerization and/or gelation step for the synthesis of the cross-linked polymers of the present invention.

The proportions of the various reaction ingredients (reactant starting materials, template, solvent) for the polymerization/gelation in the presence of template may be selected as described above for the polymerization step (as in the absence of template). The stoichiometry of the materials (i.e., monomers and/or polymers) which will form the cross-linked polymer may be important to obtaining the preferred desired cross-linked polymer, as it is in the absence of template, as described above. Useful proportion ranges of the template are 5 to 500 percent by weight (of the entire reaction mass) of template, 5 to 500 percent by weight of solvent and 5 to 500 percent by weight of the materials that will form the cross-linked polymer.

The counterions of the polyalkylamine polymer can be exchanged by adding a solvent to form a gel, adding a base such as ammonium hydroxide or NaOH to form a salt with the original counterion and to form the free-base of the polyalkylamine polymer, removing the salt by washing, and then reacidifying the polyalkylamine polymer with the conjugate acid of the desired counterion.

In processes for preparing the polymers of the present invention, there is usually some small amount of the reactants that are polymeric but not cross-linked. If it is desired to remove this uncross-linked (and therefore soluble) fraction, this can be done by extracting the polymeric ammonium salt with a solvent in which the uncross-linked polymer dissolves, such as water or methanol. The solvents used for the purification and/or ion exchange steps are those in which the materials needed for ion exchange are at least somewhat soluble and generally those that swell the polymer such as, by way of example and without limitation, the following solvents (or mixtures thereof): water, alcohols, polar protic solvents, polar aprotic solvents, solvents containing the conjugate acid of the desired counterion, solvents containing the desired base for removal of the undesired original couterion, and solvents containing salts of the desired counterions. Generally, water and one or more of the above listed bases or acids for the ion exchange step in the process are used. The solvent will be sufficiently volatile to allow relatively easy removal during drying.

The pH of the product polymer following purification and counterion exchange is generally in the range of about pH 2–8 or about pH 3–7. At pH values above the pKa of the amine groups of the polyalkylamine polymer, the gel structure of the hydrated gel will generally collapse and the polymer will have a lower swell factor. However, the presence of quaternary amine nitrogens in the polymer ensure some degree of ionization and provide some swell to the polymer.

Methods used for the separation of solids and liquids in the extraction purification of the polymeric ammonium salt product include, but are not limited to, Soxhlet extraction, filtration, centrifugation, and/or other such methods used for the separation of solids and liquids. Counter-current extraction methods may be used in the purification step. In applying such methods for the physical separation of solids and liquids, a wide variety of equipment may be employed. These include but are not limited to metal or polymer based screens, cloths, fritted or scintered glass or metal, depth filtration medium, and/or membranes. The optimal means for separation will vary according to the specific polymeric ammonium salt, the solvent and/or solvent mixture being employed, and the state of ionization of the polymer.

Cross-link density (as measured by the swell factor in water) can be controlled by judicious use of solvents, temperature and reaction time. Some solvents (e.g. $H_2O$, EtOH), when used alone, produce polymers that swell very little in water. Mixtures of solvents and solvents such as MeOH can produce highly swellable polymers. Short reaction times and/or lower temperatures produce less cross-linking and a higher degree of swelling.

Cross-linking can also be accomplished by using small amounts of tri- or higher functionality amines or halides. Cross-linking can also be accomplished by exposing the uncross-linked polymeric ammonium salt to ionizing radiation.

In the embodiment mentioned above, the polymeric ammonium salt will generally have a swell factor of at least about 4 in water. The degree of swellability of the polymer is determined by 3 major factors. One of these is the degree of salt formation in the polymer, that is what percentage of the amino nitrogen atoms present are in their salt form. The higher this percentage, the more the polymer will swell. Generally, at least 80% of the amino groups are in their salt form, or at least about 90% are in the salt form. Included within the definition of "polymeric ammonium salt" herein is a polymer where at least about 50% of the amino groups in the polymer are in their salt form. Another factor controlling swellability is the hydrophilicity of the groups between the nitrogen atoms. Generally, the more carbon atoms these groups contain, the less hydrophilic they are, and the less the polymer will swell in water. The final controlling factor is cross-link density. Typically, the higher the cross-link density, the less the polymer will swell.

The conditions during polymer synthesis and handling affect the observed swell factor. Thus, swell factor generally increases with decreasing monomer concentration in the reaction solution, undergoing a sharp increase at high dilution. The reaction time is also important. The reactants react to form higher molecular weight (MW) polymer at longer incubation times. Reaction temperature contributes to MW growth, with elevated reaction temperatures producing higher molecular weight in shorter periods of time. The workup procedure also removes low molecular weight polymer and decreases swell. Washing the product with aqueous base, then with acid, shrinks and reswells the polymer, squeezing out soluble components. A further reduction in swell is observed after continuously extracting the polymer with an organic solvent, followed by water, in a Soxhlet apparatus, for example.

The choice of solvent for the polymerization has a large effect on the swellability of the final product. A swell of essentially zero is obtained in media that do not dissolve the reactants. The observed swell factor is very low in interfacial systems in which bifunctional amine acceptor is dissolved in an organic phase and diamine is dissolved in water. The swell can be increased slightly by neutralizing the acid by-product which is generated during the polymerization reaction. The formation of higher swell polymers is promoted by solvents that dissolve both reactants, especially dipolar, aprotic solvents.

The hydrated polymer particles must be sufficiently small to pass through the apertures in the surrounding coat. The size of 50% of the hydrated polymer particles is generally about 100 microns, or in the range of about 5–800 microns. Consequently, the size of the apertures is generally in the range of about 100–20,000 microns, or about 200–3500 microns.

The size of the hydrated particles with respect to the dehydrated particles can be generally predicted. The size of the hydrated polymeric ammonium salt particles will generally be larger in aqueous media having a pH below the pKa of the protonated amine groups present in the particles than they are in media having a pH above the pKa of the protonated amine groups, e.g., the hydrated particles are generally larger in aqueous media having a pH below about 9 than they are in aqueous media having a pH above about 9. This is because the primary, secondary and tertiary amine groups of polyalkylamine polymer are not ionized above their $pK_a$'s and the polymer collapses in this media. Accordingly, the size of dry polyamine polymer particles generally range from about 2 to about 400 microns, or about 14 to about 200 microns.

Polyamine polymer particles are generally prepared using conventional particle size reduction methods, such as milling. The size reduction can be performed after or during either polymerization, purification, ion exchange and/or drying. The gel particle size reduction of the product polymer is typically accomplished during the polymerization step by mixing or agitation of the reaction in the reactor.

The particle size reduction may be done in either the wet, damp, frozen or dry state of the cross linked polymeric ammonium salt product. Mill types useful for particle size reduction include, but are not limited to, a pin mill, hammer mill, cutting mill, rotor-stator mill, media mill, attritor, jet mill, air classifying mill, opposing air jet mill, and/or sonicator. The milling may be done on either a batch, semibatch, or continuous flow through basis, the preference of either being dictated by the location of the mill step in the process, the state of the polymeric ammonium salt, the solvent content of the polymer, the degree to which the polymer is swollen, and the improvement of overall process efficiency. Depending on the specific step within the process after which the size reduction step is done, the judicious selection and use of the appropriate mill method will produce the desired particle size range polymeric ammonium salt particles.

When size reduction is done in the wet state, the solvent used for slurrying the polymer may be either a swelling or nonswelling solvent depending on the type of milling under consideration. When size reduction is done in the damp or dry state it is possible for a combination drying-milling or purification-milling operation to be done. When size reduction is done in the dry state, the polymer may be milled at several temperature ranges: cryogenic, such as liquid nitrogen or carbon dioxide; ambient; and elevated, up to about 150° C., and below temperatures which may cause significant degradation of the polymer.

The polymeric ammonium salt product of the present invention is preferably dried so as to remove solvent. By drying is meant the removal of solvent from the polymer matrix. Methods commonly used by those skilled in the art of drying may be employed. Methods for drying include, but are not limited to, tray drying, spray drying, flash drying, rotary paddle drying (either vertical or horizontal, and/or agitated drying, wherein the polymer is exposed to heat, vacuum, and/or dry gas convection to effect the removal of solvent. Other suitable methods include solvent displacement during which a higher boiling solvent is displaced with a lower boiling solvent, azeotropic distillation, or salting out during which the polymer is exposed to a solution having a high salt concentration to cause collapse, and thereby dehydration, of the hydrated gelatinous particles.

The apertures in the coat generally expose between about 1 and 75% of the core surface. The release rate of the drug from the device is a function of the number and size of the apertures. Generally, the greater the number or size of apertures, the greater the release rate of drug. In one embodiment, the coat comprises at least about 2 apertures, or about 2–1000 apertures. In another embodiment, the apertures are at least about 100 μm in diameter or about 100–20000 μm in diameter. The apertures are larger in diameter than the hydrated particles of polyalkylamine polymer.

The apertures allow liquids from the environment of use to make contact only with exposed portions of the core when in use. The number, size and configuration of the apertures is chosen to provide the release rate required to suit a pharmacologically recognized requirement since the gelatinous dispersion can form only where the apertures allow such core-liquid contact. The apertures can be formed with a laser as follows.

In one embodiment, a digital laser marking system is used to drill the holes required. This system allows for an array of apertures to be drilled on both faces of a dosage form simultaneously and at rates suitable for production of dosage forms. The process utilizes a digital laser marking system (for example the DigiMark™ variable marking system, available from Directed Energy, Inc.) to produce a variable number of holes through the surface or coating of the dosage form, at rates practically suitable for production of dosage forms. With this equipment, the steps involved in this laser drilling process are as follows: a digital laser marking system is focused at a laser stage; the dosage form is moved onto the laser stage of the digital laser marking system; the digital laser marking system is pulsed to energize those laser tubes needed to drill the desired apertures along a linear array on the dosage form; the dosage form is moved forward on the laser stage and the digital laser marking system is again pulsed as needed to produce an additional linear array of apertures; and the dosage form is then removed from the laser stage.

The apertures can be formed by any of a number of conventional methods for forming apertures in film coats. Such methods include, for example, drilling with a drill bit, or a laser-based process as disclosed in U.S. Pat. No. 5,366,738.

Absent the apertures, the coat is preferably substantially impermeable to the passage of fluid from an aqueous environment of use. Likewise absent the apertures, the coat is preferably substantially impermeable to the passage of the protonated amine drug into an environment of use. Suitable film-forming materials for the coat are selected from the group consisting of polyvinylchloride, cellulose acetate, cellulose acetate butyrate or ethylcellulose, or a combination thereof.

The impermeable wall can include: a mixture of eight parts by weight of cellulose acetate butyrate, two parts by weight of cellulose acetate and one part by weight of diethylphthalate. This mixture is dissolved in a solution of methylene chloride and methanol (about 3:1 v/v) and sprayed onto the cores to a thickness of about 250 microns. Another preferred coating consists of five parts by weight of cellulose acetate butyrate and one part by weight of triethyl citrate dissolved in a mixture of acetone and methanol (about 3:1 v/v). This mixture is sprayed on the core or dipped into the mixture so that a coating thickness of about 100 microns is applied.

The polymers used in the coating which are herein described are known to the art or can be prepared according to the procedures in Encyclopedia of Polymer Science and Technology, Vol. 3, published by Interscience Publishers, Inc., New York, in Handbook of Common Polymers by Scott, J. R. and Roff, W. J., 1971, published by CRC Press, Cleveland, Ohio.

The coating can be applied by dipping the cores into a solution of the polymer or by coating the cores using a pharmaceutically acceptable polymer coating process, such as by spray-coating the cores with a solution containing the polymer and other optional excipients. Among the groups of polymers that can provide this type of protection are cellulose acetate, cellulose acetate butyrate, ethylcellulose, polyvinylacetate, polyvinyl chloride and polymers of acrylic and methacrylic acid esters.

The polymeric coating is applied to and adheres to the entire surface of the core. The coating is applied to a thickness of from about 1 to about 1000 microns but preferably about 10 to about 500 microns typically, although thinner and thicker coatings fall within the scope of the invention. Apertures are produced in the coating to expose the core, using either a drill, a coring device or any other pharmaceutically accepted means.

Some of the materials listed above that comprise the coat may be too brittle or may have Tg values that are generally too high for use as a film-forming material. Such materials can be combined with one or more plasticizers to render them suitable. As used herein, a plasticizer is a first material that reduces the melting point, softening temperature or Tg of a film-forming material in the coat. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, NY) the disclosure of which is hereby incorporated by reference. In specific embodiments, the plasticizer is selected from the group consisting of diethylphthalate, dibutylsebacate and triethylcitrate.

The performance of a controlled release formulation according to the invention (Example 2, Formulation B) was compared to that of a controlled release formulation made according to U.S. Pat. No. 5,366,738 (Example 1, Formulation A). The key differences between the two formulations was the identity of the hydrogel polymer used and some of the pharmaceutical excipients used. The dissolution profiles of the two formulations were evaluated according Example 3. A summary of the dissolution data obtained for the formulations is include in the table below.

|  | Amount Released (% wt., Mean ± SD) | |
| --- | --- | --- |
| Time (h) | Formulation A | Formulation B |
| 0.5 | 0.8 ± 0.0 | 1.0 ± 0.2 |
| 1.0 | 1.1 ± 0.0 | 4.4 ± 0.8 |
| 2.0 | 1.7* | 11.5 ± 2.0 |
| 4.0 | 5.7 ± 0.3 | 25.1 ± 2.5 |
| 6.0 | Not determined | 42.1 ± 3.0 |
| 24.0 | 9.3 ± 1.1 | 91.3 ± 0.7 |

*indicates average of two readings.

Dissolution results of Formulation (A) tablets showed that the release rate of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidine-carboxamide) is extremely slow and did not exceed 10% at the 24 h sampling point. However the tablets of Formulation (B), which contains DMP 504, resulted in a sustained release of [S—(R,S)]-2-[4-[[(4-methyl)piperazin-1-yl]carbonyl] phenoxy]-3,3-diethyl-N-[1-(3,4-methylenedioxyphenyl) butyl]-4-oxo-1-azetidine- carboxamide) with almost complete recovery from the tablets at the 24 h time point.

Visual observations were made of the tablets after the 24 h dissolution time point. Tablets made from Formulation (A) showed clogging of the apertures which is possibly due to an interaction between [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidine-carboxamide), which is an amine, and carbopol, which is an acid, wherein an insoluble ion pair was formed and clogged the apertures in the coat. Accordingly, only a minimal amount of the [S-(R,S)]-2-[4-[[(4-methyl)piperazin-1-yl] carbonyl]phenoxy]-3,3-diethyl-N-[1-(3,4-methylenedioxyphenyl)butyl]-4-oxo-1-azetidinecarboxamide) was released. On the other hand, tablets prepared from Formulation (B) showed no clogging of the apertures and therefore provided almost complete release of the drug.

| Time (h) | Amount Release (% wt.) |
|----------|------------------------|
| 0.5      | 0–10                   |
| 1.0      | 1–20                   |
| 2.0      | 5–25                   |
| 4.0      | 10–35                  |
| 8.0      | 20–50                  |
| 12       | 30–70                  |
| 16       | 50–90                  |
| 20       | 60–95                  |
| 24       | 70–100                 |

The pharmaceutical composition, or dosage form thereof, can comprise one or more pharmaceutical excipients including, for example, a release-modifying agent, bulking agent, processing agent, antioxidant, acidifying agent, alkalizing agent, buffering agent, preservative, adsorbent, sweetening agent, antiadherent, binder, lubricant, diluent, direct compression excipient, glidant, lubricant, opaquant, polishing agent, disintegrant, flavorant, colorant, and osmotic agent.

As used herein, the term "antioxidant" is intended to mean an agent that inhibits oxidation and thus is used to prevent the deterioration of preparations by oxidation. Such compounds include, by way of example and without limitation, ascorbic acid, ascorbyl palmitate, butylated hydroxyanisole, butylated hydroxytoluene, hypophophorous acid, monothioglycerol, sodium ascorbate, sodium formaldehyde sulfoxylate and sodium metabisulfite and others known to those of ordinary skill in the art. Other suitable antioxidants include, for example, vitamin C, BHT, BHA, sodium bisulfite, vitamin E and its derivatives, propyl gallate or a sulfite derivative.

A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, ascorbic acid, and others known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "sweetening agent" is intended to mean a compound used to impart sweetness to a preparation. A sweetening agent may be included in the time-release coating or other exterior coating of the tablet. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean agents which prevent the sticking of solid formulation ingredients to punches and dies in a tableting machine, for example, during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean substances generally used to cause adhesion of powder particles in solid granulations. These materials may include the above-listed thermoformable materials. Moreover, such compounds may include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art. Other exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "diluent" is intended to mean inert substances used as fillers to create the desired bulk, flow properties, and compression characteristics in the preparation of the cores. Such compounds include, by way of example and without limitation, dibasic calcium phosphate, kaolin, lactose, sucrose, mannitol, microcrystalline cellulose (Avicel™ PH-101), powdered cellulose, precipitated calcium carbonate, sorbitol, and starch and other materials known to one of ordinary skill in the art.

As used herein, the term "direct compression excipient" is intended to mean a compound used in direct compression formulations. Such compounds include, by way of example and without limitation, dibasic calcium phosphate (e.g., Ditab) and other materials known to one of ordinary skill in the art.

As used herein, the term "dusting" is intended to mean the step of contacting a powdered pharmaceutical excipient with the solid extrudate or sized particle either prior to or during spheronization. Generally, the dusting material that adheres to the surface of the spheronized particle is less than 5% wt. of the total bead weight.

As used herein, the term "glidant" is intended to mean agents generally used in tablet or capsule formulations to reduce friction during tablet compression. Such compounds include, by way of example and without limitation, colloidal silica, cornstarch, fumed silica (Cab-O-Sil™), talc (Alphafil™ 500 USP), calcium silicate, magnesium silicate, colloidal silicon, silicon hydrogel and other materials known to one of ordinary skill in the art.

As used herein, the term "lubricant" is intended to mean substances generally used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a coating opaque. May be used alone or in combination with a colorant. Such compounds include, by way of example and without limitation, titanium dioxide and other materials known to one of ordinary skill in the art.

As used herein, the term "polishing agent" is intended to mean a compound used to impart an attractive sheen to coated cores. Such compounds include, by way of example and without limitation, carnauba wax, and white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

Exemplary osmagents or osmotic agents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

The dosage form of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation including, by way of example and without limitation, glycerylmonostearate (Imwittor™ 900), nylon, cellulose acetate butyrate, d,1-poly (lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

When included in a dosage form, the pharmaceutical composition of the invention will together comprise an effective amount of an amine drug. By the term "effective amount", it is understood that a therapeutically effective amount is contemplated. A therapeutically effective amount is the amount or quantity of drug that is sufficient to elicit the required or desired therapeutic response, or in other words, the amount that is sufficient to elicit an appreciable biological response when administered to a patient.

As used herein, "pharmaceutically acceptable salts" refer to derivatives of the disclosed compounds wherein the amine drug or polyalkylamine polymer is modified by making an acid salt thereof. Examples of pharmaceutically acceptable salts include, but are not limited to, mineral or organic acid salts of the drug. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences,* 18th Ed. (Alfonso R. Gennaro, ed.; Mack Publishing Company, Easton, Pa., 1990); *Remington: the Science and Practice of Pharmacy* 19$^{th}$ Ed.(Lippincott, Williams & Wilkins, 1995); *Handbook of Pharmaceutical Excipients,* 3$^{rd}$ Ed. (Arthur H. Kibbe, ed.; Amer. Pharmaceutical Assoc., 1999); the *Pharmaceutical Codex: Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, an "amine drug" is a drug possessing at least one ionizable or ionized nitrogen atom. The ionizable or ionized nitrogen atom is a primary, secondary, tertiary or quaternary nitrogen atom. For example, [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide), the compound of Formula 2 includes an ionizable tertiary nitrogen atom.

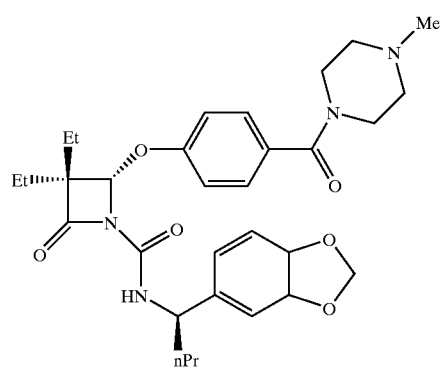

Formula 2

Suitable amine drugs that can be included in the pharmaceutical composition of the invention include, for example, other amine drugs known to those of ordinary skill in the medical or pharmaceutical sciences and which release can be controlled by a polyalkylamine polymer-based gel.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

This procedure is used to prepare tablets containing [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide), an amine drug, and a negatively charged hydrogel, not a polyalkylamine polymer. The method herein is a modified version of the method disclosed in U.S. Pat. No. 5,366,738. The following ingredients in the amounts indicated were used to prepare the tablets.

Formulation (A)

| INGREDIENT | AMOUNT (mg) |
|---|---|
| [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) | 50.0 |
| Carbopol 974p | 37.5 |
| Lactose monohydrate | 23.5 |
| Sodium phosphate (dibasic, anhydrous) | 37.5 |
| Magnesium stearate | 1.5 |

Each ingredient was sieved through a US 25 mesh screen. The [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) (12.5 g), Carbopol 974p (9.37 g), lactose monohydrate (5.87 g), and sodium phosphate (9.37 g) were mixed in a Turbula™ mixer for 10 min at 42 RPM. This blend was placed in a glass mortar and pestle, and enough of a 90% solution of ethyl alcohol in water was added to the blend to produce a wet mass. The wet mass was then sieved through a US No. 8 mesh screen and then dried overnight at 40° C. in a vacuum oven. The just formed granulate was passed through a US 25 mesh screen and mixed in a Turbula™ mixer for 10 minutes at 42 RPM. Magnesium stearate (0.375 g) was then added to the blend and mixed in the Turbula™ mixer for 5 minutes at 42 RPM. The mixture was then compressed into 150 mg ⁹⁄₃₂" diameter standard concave tablets, using an F-Press, having a hardness of approximately 8–10 SCAU. The tablets (cores) were then coated with a solution containing 4% cellulose acetate butyrate, 0.4% triethyl citrate in a solvent mixture of acetone:ethanol in a ratio of 3:1. The thickness of the applied coat was $100\mu$. Finally, 18 holes were drilled into each face of the tablet using a 0.45 mm diameter drill bit.

EXAMPLE 2

This procedure is used to prepare tablets containing [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide), an amine drug, and a polyalkylamine polymer hydrogel (DMP 504) according to the invention. The method herein is the same as the method of Example 1, except that different ingredients, and different amounts thereof, were used. The following ingredients in the amounts indicated were used to prepare the tablets.

Formulation (B)

| INGREDIENT | AMOUNT (mg) |
| --- | --- |
| [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) | 50.0 |
| DMP 504 (polyalkylamine polymer) | 75.0 |
| Microcrystalline cellulose (Avicel ® PH101) | 23.5 |
| Magnesium stearate | 1.5 |

Each ingredient was sieved through a US 25 mesh screen. The [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) (12.5 g), DMP 504 (18.75 g) and Avicel® PH 101 (5.88 g) were mixed in a Turbula™ mixer for 10 min at 42 RPM. This blend was placed in a glass mortar and pestle, and enough of a 90% solution of ethyl alcohol in water was added to the blend to produce a wet mass. The wet mass was then sieved through a US No. 8 mesh screen and then dried overnight at 40° C. in a vacuum oven. The just formed granulate was passed through a US No. 25 mesh screen and mixed in a Turbula™ mixer for 10 minutes at 42 RPM. Magnesium stearate (0.375 g) was then added to the blend and mixed in the Turbula™ mixer for 5 minutes at 42 RPM. The mixture was then compressed into 150 mg ⁹⁄₃₂" diameter standard concave tablets, using an F-Press, having a hardness of approximately 8–10 SCAU. The tablets (cores) were then coated with a solution containing 4% cellulose acetate butyrate, 0.4% triethyl citrate in a solvent mixture of acetone:ethanol having a ratio of 3:1. The thickness of the applied coat was $100\mu$. Finally, 18 holes were drilled into each face of the tablet using a 0.45 mm diameter drill bit.

EXAMPLE 3

The in vitro release of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) was evaluated for the tablets of Example 1 and Example 2 using the USP paddle dissolution apparatus. A volume of 900 ML of 0.1 M acetate buffer at a pH of 4, maintained at 37° C., was used as the dissolution media. A paddle speed of 100 RPM was employed. Serial samples were withdrawn at appropriate time intervals, filtered through a $0.45\mu$ PVDF filter and analyzed by high pressure liquid chromatography (HPLC). The withdrawn sample quantity was replaced by fresh buffer.

The HPLC analysis was conducted on a system consisting of a pump, an autoinjector (Model 717 WISP), a UV detector operated at 235 nm, and a column oven set at 50° C., all from Waters, USA. The separation was accomplished on a Nova-Pak™ C18, 15 cm length×3.9 mm i.d. column. The mobile phase consisted of acetonitrile: methanol: phosphate buffer (0.01 M, pH 7) in a ratio of 3:3:4, and was delivered at a rate of 2 mL/min. The injection volume was $20\,\mu\text{L}$. Typical retention time for [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) was about 8 minutes.

EXAMPLE 4

The same procedure used in example 2 can be followed to prepare tablets containing [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) and the free form, rather than the salt form, of the polyalkylamine polymer. A formulation prepared according to this example includes the following ingredients in the approximate amount indicated:

| INGREDIENT | AMOUNT (mg) |
| --- | --- |
| [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide) | 50.0 |
| DMP 504 (polyalkylamine polymer) free base | 62.0 |
| Microcrystalline cellulose (Avicel ® PH101) | 23.5 |
| Magnesium stearate | 1.5 |

We claim:

1. A controlled release solid dosage form comprising:
    a pharmaceutical composition comprising an amine drug, wherein the amine drug is the free base or salt form of

[S-(R,S)]-2-[4-[[(4-methyl)piperazin-1-yl]carbonyl] phenoxy]-3,3-diethyl-N-[1-(3,4-methylene-dioxyphenyl)butyl]-4-oxo-1-azetidinecarboxamide) and a polyalkylamine polymer, wherein the polyalkylamine polymer is cross-linked polymeric ammonium salt and comprises groups that link ammonium nitrogen atoms wherein:

about 25% or more of the groups which link ammonium nitrogen atoms are group Y, wherein each Y is independently —$C(R^1R^2)_b$—; b is an integer of 7 to about 20; and each $R^1$ and each $R^2$ is independently alkylene of about 1 to 20 carbon atoms;

zero to about 75% of the groups which link ammonium nitrogen atoms are group Z wherein Z is a hydrocarbylene radical containing 2 to 50 carbon atoms, the hydrocarbylene radical optionally containing or substituted with one or more hydroxyl, ether, ester, amino, thioether, keto, silyl group or helerocyclic rings;

about 25% or more of the ammonium nitrogen atoms are secondary ammonium nitrogen atoms; and said cross-linked polymeric ammonium salt is insoluble in water;

a coat surrounding the pharmaceutical composition and comprising a film-forming polymer and plasticizer; and plural apertures in the coat;

wherein the amine drug and polyalkylamine polymer are released through the apertures when the dosage form is placed into an aqueous environment of use, and the dosage form provides a controlled release of the amine drug.

2. A controlled release solid dosage form of claim 1, wherein the polyalkylamine polymer is a polymer of the Formula 1:

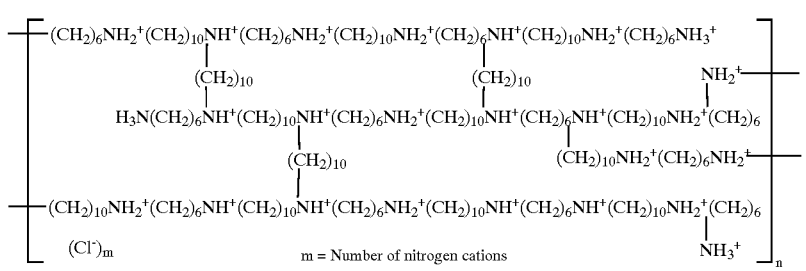

Formula I wherein n is at least one; m is at least equal to the number of quaternary amines; and the ends are independently capped with amine or hydroxyl groups.

3. The controlled release solid dosage form of claim 2, wherein the polyalkylamine polymer is DMP 503 or DMP 504.

4. The controlled release solid dosage form of claim 1, wherein the polyalkylamine polymer has a swell factor of at least about 4.

5. The controlled release solid dosage form of claim 1, wherein the polyalkylamine polymer comprises about 15–25% primary ammonium nitrogen atoms, about 40–60% secondary ammonium nitrogen atoms, about 15–25% tertiary ammonium nitrogen atoms and less than about 5% quaternary ammonium nitrogen atoms.

6. The controlled release solid dosage form of claim 1, wherein at least one nitrogen atom in the polyalkylamine polymer is further substituted with the group Q which is a hydrocarbyl group containing 1 to 50 carbon atoms, and optionally containing one or more hydroxy, ether, amino, thioether, keto, silyl groups or heterocyclic rings.

7. The controlled release solid dosage form of claim 1, wherein the polyalkylamine polymer is made in the presence of a template.

8. The controlled release solid dosage form of claim 1, wherein the amine drug is released over a period of at least 3 hours or a period of 3–24 hours after exposure to an aqueous environment.

9. The controlled release solid dosage form of claim 1, wherein the film-forming polymer is selected from the group consisting of polyvinylchloride, cellulose acetate, cellulose acetate butyrate, ethylcellulose, and a combination thereof.

10. The controlled release solid dosage form of claim 1, wherein the plural apertures are at least about 100 $\mu$m in diameter.

11. The controlled release solid dosage form of claim 1, wherein the dosage form comprises at least about 2 apertures.

12. The controlled release solid dosage form of claim 1, wherein the polyalkylamine polymer is a particulate hydrogel that forms hydrated particles when exposed to an aqueous environment.

13. The controlled release solid dosage form of claim 12, wherein 50% of the hydrated particles are about 100 $\mu$m in diameter.

14. The controlled release solid dosage form of claim 1, wherein the amine drug is released into an environment of use according to a release profile approximating the following:

| Time (h) | Amount Release (% wt.) |
|---|---|
| 0.5 | 0–10 |
| 1.0 | 1–15 |
| 2.0 | 5–25 |
| 4.0 | 10–30 |
| 8.0 | 20–50 |
| 12 | 30–70 |
| 16 | 50–90 |
| 20 | 60–95 |
| 24 | 70–100 |

15. The controlled release solid dosage form of claim 1, wherein the plasticizer is selected from the group consisting of diethylphthalate, dibutylsebacate, or triethylcitrate.

16. The controlled release solid dosage form of claim 1, wherein the pharmaceutical composition further comprises at least one pharmaceutical excipient selected from the group consisting of a release-modifying agent, bulking agent, processing agent, antioxidant, acidifying agent, alkalizing agent, buffering agent, preservative, adsorbent, sweetening agent, antiadherent, binder, lubricant, diluent, direct compression excipient, glidant, lubricant, opaquant, polishing agent, disintegrant, flavorant, colorant, and osmotic agent.

17. The controlled release solid dosage form of claim 1, wherein the film-forming material forms an impermeable water insoluble coat.

18. A pharmaceutical composition comprising:
an amine drug, wherein the amine drug is the free base or salt form of [S-(R,S)]-2-[4-[[(4-methyl)piperazin-1-yl]carbonyl]phenoxy]-3,3-diethyl-N-[1-(3,4-methylenedioxyphenyl)butyl]-4-oxo-1-azetidinecarboxamide);
a gel-forming polyalkylamine polymer, wherein the polyalkylamine polymer is cross-linked polymeric ammonium salt and comprises groups that link ammonium nitrogen atoms wherein:
about 25% or more of the groups which link ammonium nitrogen atoms are group Y, wherein each Y is independently —C($R^1R^2$)$_b$—; b is an integer of 7 to about 20; and each $R^1$ and each $R^2$ is independently alkylene of about 1 to 20 carbon atoms;
zero to about 75% of the groups which link ammonium nitrogen atoms are group Z wherein Z is a hydrocarbylene radical containing 2 to 50 carbon atoms, the hydrocarbylene radical optionally containing or substituted with one or more hydroxyl, ether, ester, amino, thioether, keto, silyl group or heterocyclic rings;
about 25% or more of the ammonium nitrogen atoms are secondary ammonium nitrogen atoms; and said cross-linked polymeric ammonium salt is insoluble in water; and
at least one pharmaceutical excipient;
wherein the polyalkylamine polymer controls the release of the amine drug when the pharmaceutical composition is included in a dosage form and exposed to an aqueous environment of use.

19. The pharmaceutical composition of claim 18, wherein the polyalkylamine polymer is a polymer of the Formula 1:

21. The pharmaceutical composition of claim 18, wherein the polyalkylamine polymer has a swell factor of at least about 4.

22. The pharmaceutical composition of claim 18, wherein the polyalkylamine polymer comprises about 15–25% primary ammonium nitrogen atoms, about 40–60% secondary ammonium nitrogen atoms, about 15–25% tertiary ammonium nitrogen atoms and less than about 5% quaternary ammonium nitrogen atoms.

23. The pharmaceutical composition of claim 18, wherein at least one nitrogen atom in the polyalkylamine polymer is further substituted with the group Q which is a hydrocarbyl group containing 1 to 50 carbon atoms, and optionally containing one or more hydroxy, ether, amino, thioether, keto, silyl groups or heterocyclic rings.

24. The pharmaceutical composition of claim 18, wherein the polyalkylamine polymer is made in the presence of a template.

25. The pharmaceutical composition of claim 18, wherein the polyalkylamine polymer is a particulate hydrogel that forms hydrated particles when exposed to an aqueous environment.

26. The pharmaceutical composition of claim 25, wherein 50% of the hydrated particles are about 100 μm in diameter.

27. The pharmaceutical composition of claim 18, wherein the at least one pharmaceutical excipient selected from the group consisting of a release-modifying agent, bulking agent, processing agent, antioxidant, acidifying agent, alkalizing agent, buffering agent, preservative, adsorbent, sweetening agent, antiadherent, binder, lubricant, diluent, direct compression excipient, glidant, lubricant, opaquant, polishing agent, disintegrant, flavorant, colorant, and osmotic agent.

28. A method of treating rheumatoid arthritis with an amine drug comprising the step of administering to a subject the dosage form of claim 1.

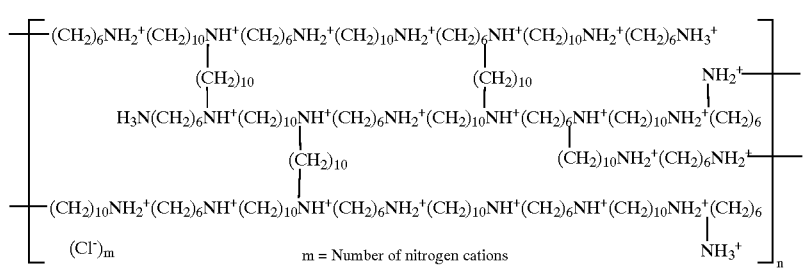

Formula I wherein n is at least one; m is at least equal to the number of quaternary amines; and the ends are independently capped with amine or hydroxyl groups.

20. The pharmaceutical composition of claim 19, wherein the polyalkylamine polymer is DMP 503 or DMP 504.

29. A method of treating rheumatoid arthritis with an amine drug comprising the step of administering to a subject the pharmaceutical composition of claim 18.

* * * * *